(12) United States Patent
Jennewein et al.

(10) Patent No.: US 9,005,939 B2
(45) Date of Patent: Apr. 14, 2015

(54) PROTOILLUDENE SYNTHASE

(71) Applicant: Fraunhofer-Gesellschaft zur Förderung der angewandten Forschung e.V., Munich (DE)

(72) Inventors: Stefan Jennewein, Aachen (DE); Benedikt Engels, Aachen (DE); Torsten Grothe, Bochum (DE); Marc Stadler, Niederkirchen (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 191 days.

(21) Appl. No.: 13/756,057

(22) Filed: Jan. 31, 2013

(65) Prior Publication Data

US 2013/0204034 A1     Aug. 8, 2013

Related U.S. Application Data

(63) Continuation of application No. PCT/EP2011/063048, filed on Jul. 28, 2011.

(30) Foreign Application Priority Data

Aug. 2, 2010   (EP) .................................... 10171576

(51) Int. Cl.
*C12N 9/88*     (2006.01)
(52) U.S. Cl.
CPC ....................................... *C12N 9/88* (2013.01)

(58) Field of Classification Search
None
See application file for complete search history.

(56) References Cited

PUBLICATIONS

Engels et al., "Cloning and Characterization of an *Armillaria gallica* cDNA Encoding Protoilludene Synthase, Which Catalyzes the First Committed Step in the Synthesis of Antimicrobial Melleolides," *Journal of Biological Chemistry* 286(9):6871-6878 (Mar. 4, 2011).
International Search Report and Written Opinion from the parent PCT Application No. PCT/EP2011/063048 (mailed Oct. 10, 2011).
Momose et al., "Melleolides K, L, and M, New Melleolides from *Armillariella mellea*," *Journal of Antibiotics* 53(2):137-143(Feb. 2000).
Oppolzer and Nakao, "Synthesis of (±)-6-Protolludene and (±)-3-EPI-6-Protoilludene by Intramolecular Magnesium-ENE- and Ketene/Alkene Addition Reactions," *Tetrahedron Letters* 27(45):5471-5474 (Jan. 1, 1986).
International Preliminary Report on Patentability from the parent PCT Application No. PCT/EP2011/063048, 8 pages (mailed Feb. 5, 2013).

*Primary Examiner* — Nashaat Nashed
(74) *Attorney, Agent, or Firm* — Klarquist Sparkman, LLP

(57) ABSTRACT

The present invention relates to an isolated, recombinant or synthetic polynucleotide encoding a polypeptide with protoilludene synthase activity and comprising a sequence selected from the group consisting of a) SEQ ID Nos. 1 or 14 of the attached sequence listing; b) a nucleic acid sequence complementary to SEQ ID Nos. 1 or 14; c) nucleic acid sequences which hybridize under stringent conditions to the nucleic acid sequences defined in a) and b) or their complementary strands, as well as to the polypeptide encoded by the isolated polynucleotide, as well as a method for the production of melleolides employing the polynucleotide or polypeptide of the invention.

15 Claims, 7 Drawing Sheets

Fig. 4A

```
                *         20          *          40          *          60          *          80
Pro1 : ---------MSQR IFLPDTLANMQWRHLNPHYAEVKKASAAWAKSFRAFQTKAQEAF----------DRCDFNI-------LASFAYPLADFARLRSGC :  74
Cop3 : MSTPSISSLTTDESPASFILPDLVSHCPFPLRYHPKGDEVAKQTVHMLDSNCPDLTAKERKAMYGIQAGFLTGYCYPTTPERLRVA :  87
Cop5 : MVGSYTGKIHVPALLESWPWFAAINPLYEQVQEESTSWFRKFDLYRDRIKKQAHDHLDTAKFG--------ASVC-PKADYALLRLAT :  80

*         100         *         120         *         140         *         160
Pro1 : DLMNIFEVIDEYSDVSTEEVRAQKDIVMDARNTEKPR------WIGGEVSRQFWD--IAKKTASTQAQKRFIDTFPEYLE : 152
Cop3 : DFLNYLFHLDNISDGMMTRETAVLADVVMNAIWFPEDYR----PAGE-----PTK--GQAAEELNPGKIARDFWSRCIPDCGPGIQARFKE : 163
Cop5 : DYLHILGFWIDYEFDTSPSDVIRQLTESIAHLLESG-DPRLDSSSSPQSHIA----CMEILRDFRKRIETFNPSQEDLRRFVKEYIRGFLE : 163

*         180         *         200         *         220         *         240
Pro1 : SVVQQAADRNNSHVRGIESYLEVRRNTIGAKPSFALLEFDMQIPDESHQSSGYQRNIRKSQIDMILGNDVVSYNLEQARDDGHNI : 239
Cop3 : TFGSFFEAVNIQARARDEGVIPDLESYIDVRRDTSGCKPCWVIIEYAL-GIDLPDFVVEHPVIAALNQGTNDLVTWSNDIFSYNVEQ : 249
Cop5 : AELTQAIDHENKVIRDIESYLSIRRSTIALRPGIALLGLALGIPQEIL-DDPYTDTITNACLDMVIIQNDAYSWNVEQVRKADGHNI : 249

*         260         *         280         *         300         *         320
Pro1 : VTIAMNEIRTDVAGAMIWVDEYHKQLESRFME------NFKKIVPRWGGPIDLQVARYCDGIGNWRANDQWSFESERYFGKKGPE : 318
Cop3 : SKGDTHNMILLMEHIGHTLQSAVDYVGSLCQQTINTFCENKQQLPSWGPEIDDMVAKYVQGIJEDWIVGSLHWSFQTRRYFGDEGQE : 336
Cop5 : ITVLMKQRDIDVQEAYEHAAQLHRETQEHFLEL-------HAKRPDWGNEGSIQA--EFDGLGEFVRGVDEWS : 313

*         340         *         360         *         380         *         400         *         420
Pro1 : IIQRR------ : 323
Cop3 : IKQHFRLVKLLTVAPPPPPPTPPPQSSDADTKKQKVKAQDGKGPVSDEEVWALVRAEQSKGSILESLFGFLTTSLSRIFFGYFFAY : 423
Cop5 : --------- : -

*         440         *         460         *         480         *         500         *         520
Pro1 : ----WITLMPKMVSEELGPQIVDGFHL-------- : 346
Cop3 : SH-------- : 425
Cop5 : SMCLGEHALSVGAGFLK : 330
``` ative patent application PCT/EP2011/063048, filed on Jul. 28, 2011 designating the U.S., which international patent application has been published in English language and claims priority from European patent application EP 10 171 576.1, filed on Aug. 2, 2010. The entire contents of these priority applications are incorporated herein by reference.

BACKGROUND OF THE INVENTION

The present invention relates to a newly identified polynucleotide as well as to the polypeptide encoded for by the polynucleotide, and to their production and uses, as well as their variants and their uses. In addition, the present invention relates to a method for producing melleolides and related fungal sesquiterpenoids aryl esters by using the newly identified polynucleotide/polypeptide.

Melleolides are characteristic secondary metabolites produced by the homobasidiomyceste genus *Armillaria*, the species of which are not only regarded as edible mushrooms, but many species are notorious forest parasites, reflecting their ability to form rhizomorphs that allow them to grow across nutrient-poor areas.

Melleolides are protoilludene type sesquiterpenoids and have a potent antimicrobial and cytotoxic activity. Up to now, there are approximately 50 known melleolides and they are almost exclusively produced by this fungal genus. Each molecule comprises a tricyclic sesquiterpenoid skeleton linked to an orsellinic acid-like polyketide side chain via an ester bond. The biosynthesis of protoilludene is thought to involve cyclization of the universal sesquiterpenoid precursor farnesyl diphosphate to protoilluden followed by further modification by cytochrome P450 monooxygenases and subsequent attachment of the polyketide side chain.

Whilst the biosynthesis of some terpenes, in particular of plants origin—like menthol, artemisinin or taxol—have been extensively studied in the past, little is known about the synthesis of the vast majority, in particular of terpenes produced by fungi.

The biosynthesis of all terpenes begins with the cyclization and rearrangement of one of three universal precursors, geranyl diphophate, farnesyl diphosphate, or geranylgeranyl diphosphate, to yield monoterpenoids, sesquiterpenoids or diterpenoids, respectively. These cyclization reactions, which are catalyzed by terpene synthases, are among the most complex chemical reactions known in nature.

Generally, plant and fungal terpene synthases show only low level of sequence identity, and whereas several terpene synthases have been isolated from plants, only a few have been reported from microbes. Also, only a very limited number of fungal sesquiterpenoid synthases have been cloned and functionally characterized, including, e.g., trichodiene synthase, aristolochene synthase, and presilphiperfolan-8b-ol synthase. Furthermore, six sesquiterpene synthases from *Coprinopsis cinerea* (*Coprinus cinereus*) yielding germacrene A, α-muurolene, δ-cadinene and α-cuprenene as major products have recently been characterized.

The biosynthesis of protoilludene type sesquiterpenoids—also known as melleolides, see above—is thought to involve cyclization of the universal sesquiterpenoid precursor farnesyl diphosphate to protoilluden followed by further modification by cytochrome P450 monooxygenases and subsequent attachment of the polyketide chain.

Since in particular melleolides, in medicine, are of high interest due to their antimicrobial and cytotoxic activity, it would be desirable to have them specifically produced or enriched in a controlled way.

SUMMARY OF THE INVENTION

Thus, it is an object of the present invention to provide for a new tool by means of which a targeted production, either homologous or heterologous, can be achieved.

SEQUENCE LISTING

The Sequence Listing is submitted as an ASCII text file [7291-90556-01_Sequence_Listing.txt, Jan. 30, 2013, 20.7 KB], which is incorporated by reference herein.

BRIEF DESCRIPTION OF THE DRAWINGS

Several embodiments of the invention are illustrated in the figures and explained in more detail in the following description. In the figures.

Figure 1:
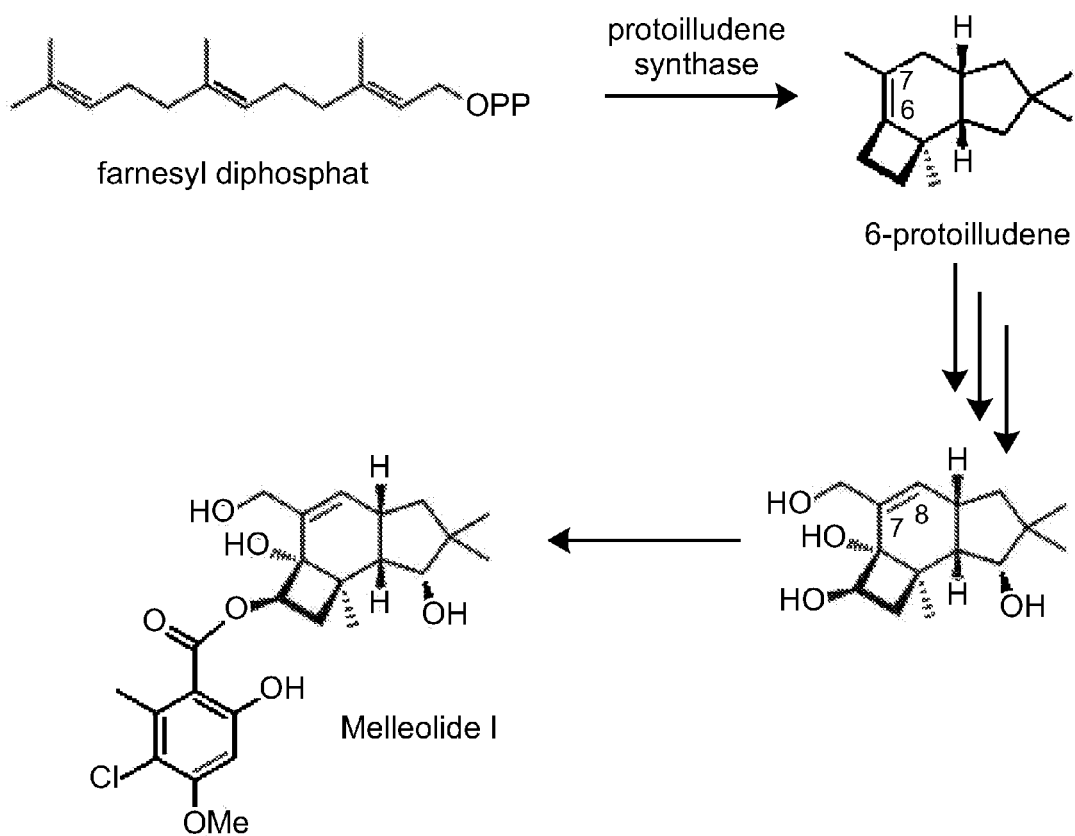
FIG. 1 shows a scheme of melleolide I biosynthesis, involving the cyclization of farnesyl diphosphate to 6-protoilludene, oxygenation reactions and the side chain attachment.

According to the invention, this and other objects are achieved by providing an isolated or synthetic or recombinant polynucleotide encoding a polypeptide with protoilludene synthase activity and comprising a sequence selected from the group consisting of:

a) SEQ ID No. 1 or 14 of the attached sequence listing;
b) a nucleic acid sequence complementary to SEQ ID No. 1 or 14;
c) nucleic acid sequences which hybridize under stringent conditions to the nucleic acid sequences defined in a) and b) or their complementary strands.

The objects are further achieved by the use of said polynucleotide or the polypeptide encoded by the polynucleotide for producing melleolides, and by a respective method for producing melleolides.

The objects are completely achieved in that way.

The above mentioned polynucleotide encodes a polypeptide with Protoilludene synthase activity, which has—according to the inventors' knowledge—been identified, purified and enzymatically characterized for the first time. This newly identified polynucleotide catalyzes the cyclization of farnesyldiphosphate to protoilludene, the step of which represents the crucial step in the synthesis of melleolides production. Thus, by having identified the gene encoding the protoilludene synthase a valuable and effective tool has been found and generated to influence the production of melleolides, e.g. by overexpressing the newly identified gene in order to generate multiple copies of the protoilludene synthase, by means of which the cyclization rate in the melleolides synthesis is elevated, and, thus, the production of melleolides increased. In that way, highly enriched melleolides may be gained, which are potent antimicrobial and cytotoxic substances and may be used as therapeutic tools in all different fields of treatment and medicine.

According to the present invention, the term "poylnucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. Also, "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. Polypeptides may be branched or cyclic, with or without branching. Cyclic, branched and branched circular polypeptides may result from post-translational natural processes and may be made by entirely synthetic methods, as well.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Similarly, a "synthetic" sequence, as the term is used herein, means any sequence that has been generated synthetically and not directly isolated from a natural source. "Recombinant" means genetically engineered DNA prepared by transplanting or splicing genes from one species into the cells of a host organism of a different species. Such DNA becomes part of the host's genetic makeup and is replicated.

The term "polynucleotide encoding a polypeptide" as used herein encompasses polynucleotides that include a sequence encoding a polypeptide of the invention, particularly protoilludene synthase of *Amillaria gallica*, having the amino acid sequence as set forth in SEQ ID No. 2. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

In addition, the term "Host cell" is presently defined as a cell which has been transformed or transfected, or is capable of transformation or transfection by an exogenous polynucleotide sequence.

According to an embodiment of the invention, the isolated polynucleotide consists of the SEQ ID No. 1 or 14 and encodes a polypeptide with protoilludene synthase activity. SEQ ID No. 1 represents the genomic sequence, whilst SEQ ID No. 14 represents the cDNA.

SEQ ID Nos. 1 and 14 as disclosed in the attached sequence listing are the genomic sequence and the cDNA, respectively, of the protoilludene synthase as identified and characterized from *Amillaria gallica*. It is to be understood that also variants thereof, which have at least a sequence identity of 90%—and that might even be found in other *Amillaria* species—are also suitable and part of the invention, since with the newly indentified protoilludene synthase a valuable tool is provided by means of which similar protoilludene synthases, i.e. protoilludene synthases that slightly differ from SEQ ID Nos. 1 or 14, may be identified by sequence comparison and subsequent enzymatically testing.

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such polypeptides using RNAs derived from the DNA constructs of the invention.

Thus, and in addition, the invention also concerns a vector, containing a nucleic acid sequence as defined above, encoding a polypeptide with protoilludene activity, the nucleic acid sequence being operably linked to control sequences recognized by a host cell transformed with the vector. According to one aspect of the invention, the vector is an expression vector, and, according to another aspect, the vector can be present in the form of a plasmid, cosmid, phage, liposome, or virus.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., Basic Methods in Molecular Biology, (1986), and Sambrook et al., Molecular Cloning: A Laboratory Manual, 2nd Ed., Cold Spring Harbor Laboratory Press, Cold Spring Harbor, N.Y. (1989).

Thus, the polynucleotide according to the invention, may, e.g., be comprised in a vector which is to be stably transformed/transfected into host cells. In the vector, the polynucleotide of the invention is under control of an inducible promoter, so that the expression of the gene/polynucleotide can be specifically targeted, and, if desired, the gene may be overexpressed in that way.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., see above.

In view of the above, the invention also concerns an isolated, recombinant or synthetic polypeptide consisting of an amino acid sequence selected from the group consisting of:
(a) an amino acid sequence shown in SEQ ID NO: 2;
b) an amino acid sequence of an allelic variant of an amino acid sequence shown in SEQ ID No. 2, wherein said allelic variant is encoded by a nucleic acid molecule that hybridizes under stringent conditions to the opposite strand of a nucleic acid molecule shown in SEQ ID No. 1 or 14;
c) an amino acid sequence of an ortholog of an amino acid sequence shown in SEQ ID No. 2, wherein said ortholog is encoded by a nucleic acid molecule that hybridizes under stringent conditions to the opposite strand of a nucleic acid molecule shown in SEQ ID No. 1 or 14; and
(d) a fragment of an amino acid sequence shown in SEQ ID No. 2, wherein said fragment comprises at least 10 contiguous amino acids.

Also, the invention refers to a host cell containing a vector as defined above and in particular a host cell which is selected from the group consisting of fungi including yeast, bacteria, insects, animal and plant cells.

According to another aspect of the invention, a host cell is used, with the nucleic acid encoding the polypeptide with protoilludene synthase activity being adapted to the codon usage of the respective host cell.

According to another embodiment of the invention, the host cell is a homobasidiomycete, in particular a homobasidiomyceste of the genus *Armillaria*, in particular *Armillaria gallica*, *Armillaria mellea*, *Armillaira ostoyae*, and other members of the genus *Armillaria*.

Yet another aspect of the invention concerns a method for producing melleolides comprising the steps of:
a. growing, under suitable nutrient conditions permissive for the production of the Melleolides, a host cell as defined claimed above; and
b. isolating said Melleolides from the host cell or the medium of its growth.

According to an aspect of the invention, the melleolide is selected from melleolide I, armillaridine, melleolide A, melleolide F, melleolide B, melleolide K, armillyl evernitate, armillarin, arnamiol, melleolide J, armillarivin, 10-alpha-hydroxy-melleolide, armillyl orsellinate, melleolide E, 1-O-trifluoroacetyl-melleolide E, melleolide H, 5'-O-methyl-melledonal, melledonal, arnamial, melleolide C, melleolide D, melledonal A, melledonal C, melledonol.

According to yet another aspect, the method comprising the above mentioned steps consist of the following steps:
i. growing, under suitable nutrient conditions, host cells transformed or transfected to comprise a nucleic acid sequence selected from a) SEQ-ID-No. 1 or 14 from the enclosed sequence protocol, b) a nucleic acid sequence complementary to SEQ ID No. 1 or 14, and c) nucleic acid sequences which hybridize under stringent conditions to the nucleic acid sequences defined in a) and b) or their complementary strands;
ii. overexpressing the nucleic acid sequence;
iii. thus, enhancing melleolides production in the host cell, and
iv. isolating said melleolides from the host cell or the medium of its growth.

With the disclosed method and the targeted overexpression of the protoilludene synthase it is possible to accumulate melleolides in the host cell or in the medium the host cells are contained in. It is to be understood that it lies within the skill and knowledge of a person skilled in the art, to supplement the host cell(s) or host cell culture with additional and/or essential precursors or other substances, nutrients or metabolites that might be necessary to complete or assist the enhanced melleolides production.

Accordingly, the present invention also relates to melleolides obtained by the method as defined above. The thus generated melleolides can be efficiently used as medicaments, e.g., for treating any bacteria-caused infection or disease.

In view of the above, the invention also refers to the use of a polynucleotide, the vector, or the polypeptide as defined above, respectively, for the production of melleolides.

It is to be understood, that the production of melleolides according to the invention can be performed by means of a heterologous or homologous overexpression of the polynucleotide encoding for protoilludene synthase. Systems and methods, as well as the respective suitable host cells will be apparent to those skilled in the art upon reading the teaching of this invention.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

DESCRIPTION OF PREFERRED EMBODIMENTS

In FIG. 1, a plausible scheme of melleolide I biosynthesis is shown, involving the cyclization of farnesyl diphosphate to 6-protoilludene, oxygenation reactions and the side chain attachment.

Example 1

Generation of Protein Extracts

*Armillaria gallica* strain FU02472 was established from basidiocarps collected near Traunsee, Austria, and was propagated in submerged culture in batches of 500 mL Erlenmeyer shake flasks containing 200 mL of YMG medium at 23° C. with agitation at 140 rpm. Mycelia were harvested from the culture broth by filtration, shock-frozen with liquid nitrogen and stored at −80° C. *Escherichia coli* strain TOP10 (Invitrogen, Karlsruhe, Germany) was used for cloning and strain BL21 (DE3) CodonPlus (Agilent, Karlsruhe, Germany) was used for heterologous protein expression, along with the Gateway™ compatible vector pDEST14 (Invitrogen).

To produce protein extracts from *Armillaria*, *A. gallica* cell culture was disrupted in the mortar frozen with liquid nitrogen. Five volumes of extraction buffer (50 mM MES, 20 mM $MgCl_2$, 5 mM 2-mercaptoenthanol, 10% (v/v) glycerol and 0.1 g/g mycelia PVPP, pH 6.5) were added to the powder. After additional treatment with an Ultraturrax (12.000 rpm for 1 min) the protein extract was cleared by centrifugation (5.000 rpm for 10 min at 4° C.). The protein concentration was determined by Quick Start Bradford Protein Assay (Biorad). All protein quantification assays were done in triplicates.

*Escherichia coli* protein extracts were prepared by resolving the cell pellet from cultivation in the described extraction puffer and cells were lysed under constant cooling by two rounds of Microfluidizer treatment.

Protoilludene synthase activity was determined using [1-$^3$H]-farnesyl diphosphate (PPP) (20 Ci/mmol) (Biotend) in assay buffer (50 mM MOPS, 20 mM $MgCl_2$, 5 mM 2-mercaptoethanol, pH 7.2). Standard protoilludene synthase activity measurements were performed with 500 nM of [1-$^3$H]-FPP for 2 min followed by quenching with ethyl acetate. Part of the organic extract was then spotted onto silica-gel TLC plates and separated using 9:1 cyclohexane:ethyl acetate as the solvent, prior to analysis in a radio-TLC reader (Raytest, Straubenhardt). For the determination of $K_M$ values the reactions were stopped by quenching with 100 mM EDTA (final concentration) followed by extraction with n-pentane, purification by silica gel column chromatography and quantitation by liquid scintillation counting. All kinetic activity assays were performed in triplicate. Mass spectrometry analysis of solvent extracts was performed on a QP2010S quadrupole mass spectrometer (Shimadzu) equipped with an Rxi™-5 ms (0.25 mm ID, 30 m length) column (Restek) using the following temperature program: 80° C. for 20 min, followed by heating the column at an rate of 15° C./min to 300° C. with a final constant temperature of 300° C. for 4 min. Fragmentation was achieved by electric ionization at 1 keV.

Example 2 cDNA Library Construction and Sequencing

An *A. gallica* CloneMiner™ cDNA library (Invitrogen) was constructed according the manufacturer's protocol using cesium chloride-density-gradient and *A. gallica* strain FU02472 mRNA purified by Oligotex (Qiagen, Hilden). Recombinant *E. coli* were selected on 2YT-agar plates containing 50 μg/mL kanamycin, and 2800 randomly-picked colonies were transferred to 96-well microtiter plates containing 200 μL 2YT medium per well, with 50 μg/mL kanamycin for selection. The plates were incubated at 37° C. with continuous shaking at 160 rpm for approx 12 h. *A. gallica* cDNAs were amplified directly from the culture using forward primer 5'-CTC GCG TTA ACG CTA GCA TGG ATG-3' (SEQ ID No. 3) and reverse primer 5'-GTG AGT CGT ATT ACA TGG TCA TAG CTG-3' (SEQ ID No. 4). PCR products were cleaned and sequenced (Fraunhofer IME Aachen, Functional and Applied Genomics Group) using primer 5'-CGA CGG CCA GTC TTA AGC TCG GGC-3' (SEQ ID No. 5) on an Applied Biosystems 3730 DNA Analyzer. Sequence data were analyzed using CLC Combined Workbench 3 software (CLC bio), the Lasergene Package (DNASTAR) NCBI BLASTx and Local BLAST.

Example 3

Heterologous Expression of *A. Gallica* Protoilludene Synthase in *E. coli*

Where cDNA sequencing identified potential terpene synthase clones, the corresponding pENTRY vectors were used in LR recombination reactions involving the pDEST14 destination vector. The resulting expression constructs were then introduced into *E. coli* BL21 (DE3) Codon plus cells (Stratagene) for heterologous expression. Recombinant bacteria were cultivated in Ferenbach-baffled flasks and were induced with 1 mM IPTG when the $OD_{600}$ reached 0.5. The induced bacteria were maintained at 28° C. for 8 h with constant shaking at 160 rpm. Cells were then harvested by centrifugation, resuspended in protoilludene assay buffer and lysed using a microfluidizer.

Example 4

Genomic DNA Isolation and Southern Blot Hybridization

*A. gallica* genomic DNA was isolated using the cetyltrimethylammonium bromide (CTAB) method, and 120 µg was digested with 50 units of BamHI, EcoRI or HindIII (NEB Biolabs) as appropriate, for 8 h. The digested DNA was fractionated by 0.7% agarose gel electrophoresis at a constant 50 V overnight, transferred to a positively charged nylon membrane (Roche) and prehybridized with Roti®-Hybri-Quick (Roth) containing single stranded salmon sperm DNA. Two nucleic acid probes (~400 bp) were synthesized by PCR using forward primer 5'-CCT TCC TGA TAC TCT TGC CAA CTG-3' (SEQ ID No. 6) and reverse primer 5'-CCT CCT CCG TCG AGA CGT CCG AGT AC-3' (SEQ ID No. 7) for probe 1, and forward primer 5'-GTC ATC AAT CAT CCG GTT ATC AAA G-3' (SEQ ID No. 8) and reverse primer 5'-CTT GGG CAT CAG CGT TAT CCA CCT C-3' (SEQ ID No. 9) for probe 2. These products were labelled with $\alpha$-$^{32}$P-dATP (Hartmann Analytic) using the DecaLabel™ DNA Labeling Kit (Fermentas) according to the manufacturer's recommendations.

Example 5

Isolation of an *A. Gallica* Protoilludene Synthase Genomic Clone

The genomic clone encompassing the *A. gallica* protoilludene synthase gene was isolated by amplifying 100 ng of *A. gallica* genomic DNA using forward primer 5'-GGG GAC AAG TTT GTA CAA AAA AGC AGG CTT CGA AGG AGA TAG AAC CAT GTC TCA ACG CAT CTT CCT TCC TG-3' (SEQ ID No. 10), reverse primer 5'-GGG GAC CAC TTT GTA CAA GAA AGC TGG GTT TAG AGA TGA AAT CCG TCA ACA ATT TGA GG-3' (SEQ ID No. 11) and Herculase® II Fusion DNA Polymerase (Stratagene) in a 50-µl reaction. The PCR product was purified and sequenced as described above

Example 6

Results and Discussion

Figure 2:
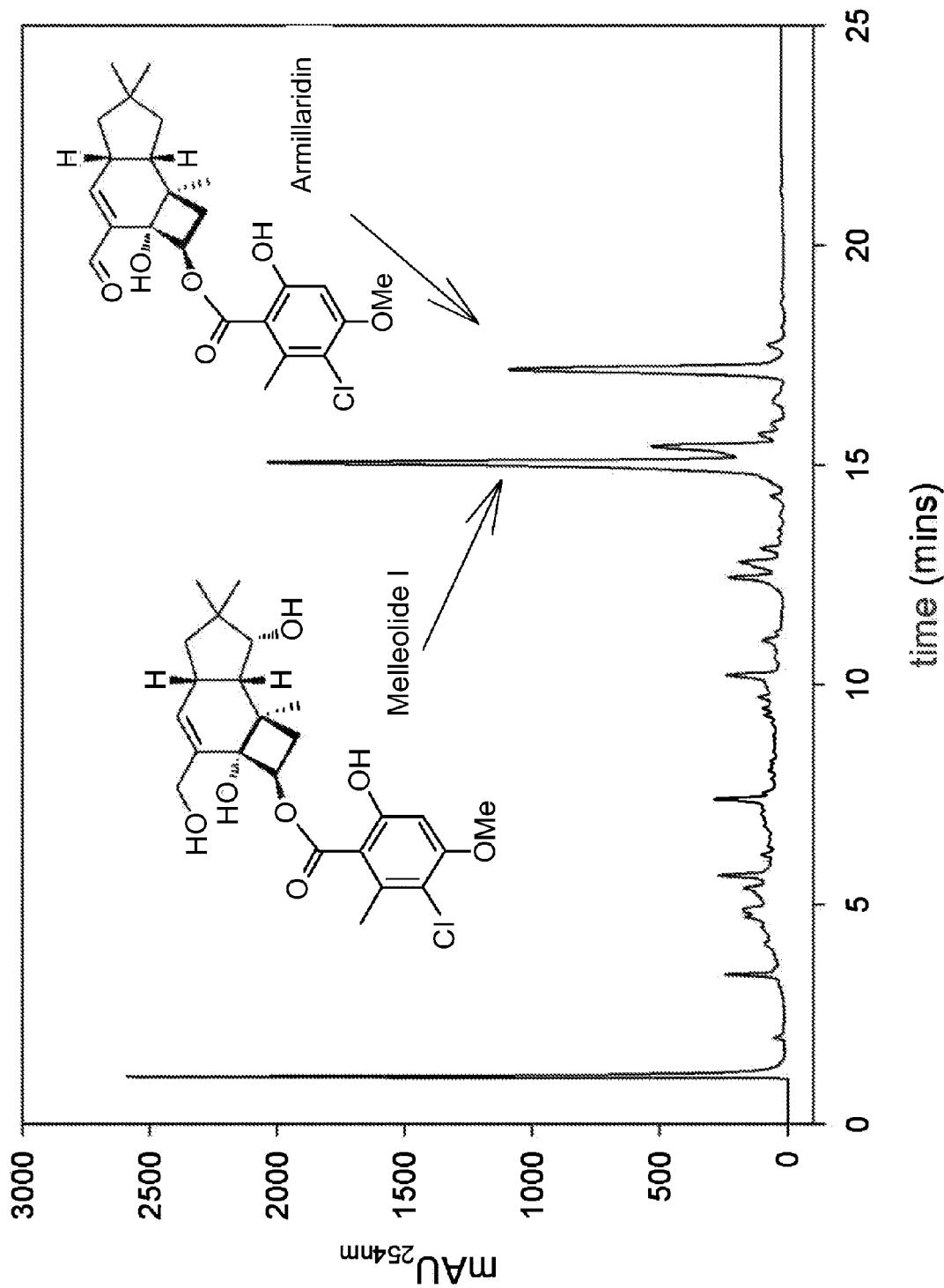
FIG. 2 shows the HPLC analysis of *A. gallica* strain FU02472 submerged culture organic extract. Using available standards two of the observed compound peaks were identified as melleolide I and armillaridin.
Figure 3A:
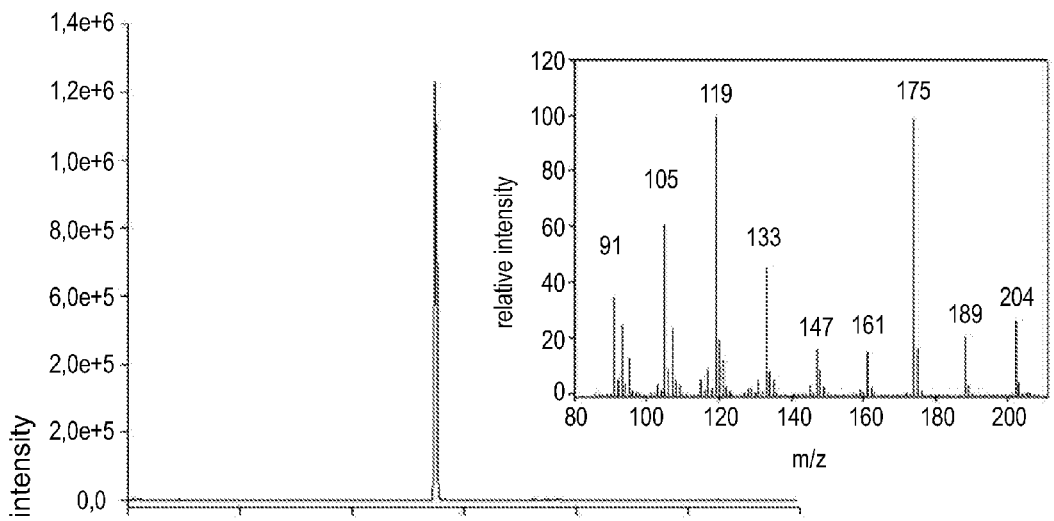
FIG. 3A-3F shows non-radioactive and radioactive test assays to confirm that the Pro1 clone expressed in *E. coli* has protoilludene synthase activity. A/B) Gas chromatograms showing a peak at retention time 8.77 min with characteristic mass spectra. A) Extract from *E. coli* clone expressing Pro1. B) Extract from *A. gallica* mycelia. C-F) RadioTLC assays: dash/dot line is start, dashed line is solvent front. C) *E. coli* pUC19 negative control. D) *E. coli* Pro1 clone incubated with [1-$^3$H]-GGPP, substrate for diterpene synthases. E) *E. coli* Pro1 clone incubated with [1-$^3$H]-FPP. F) *A. gallica* positive control.
Figure 3B:
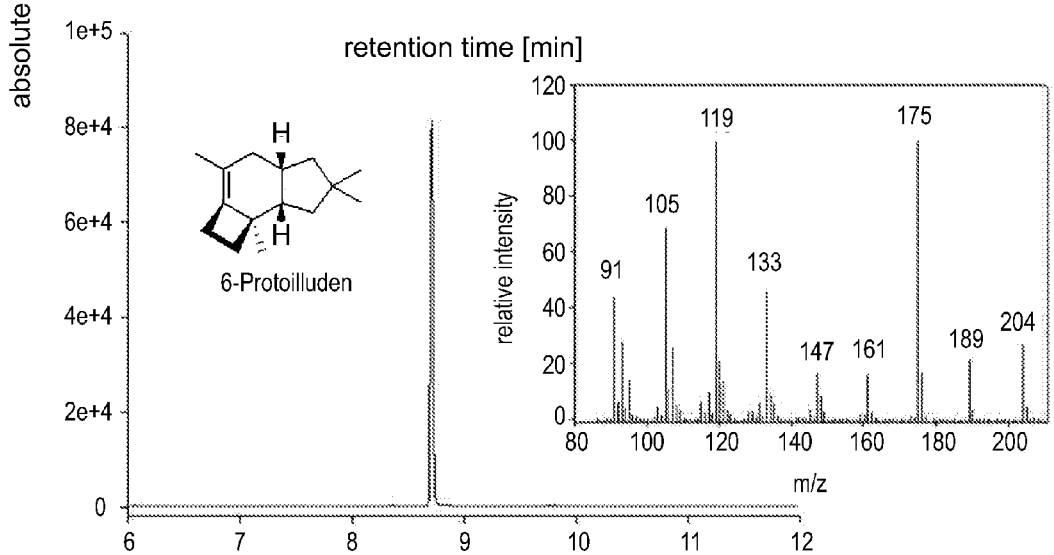
Figure 3C:
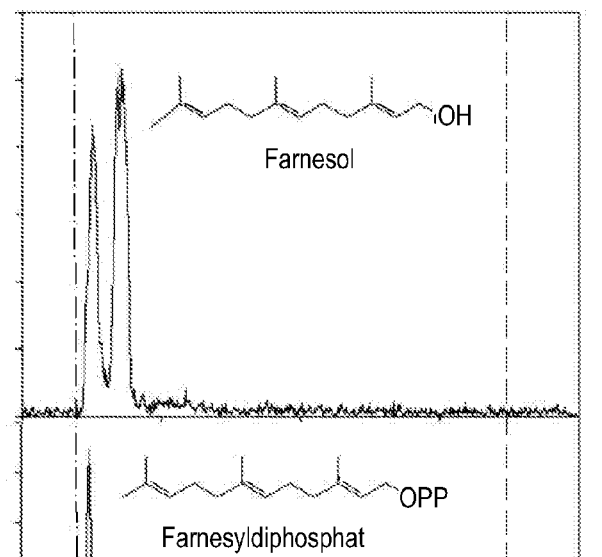
Figure 3D:
Figure 3E:
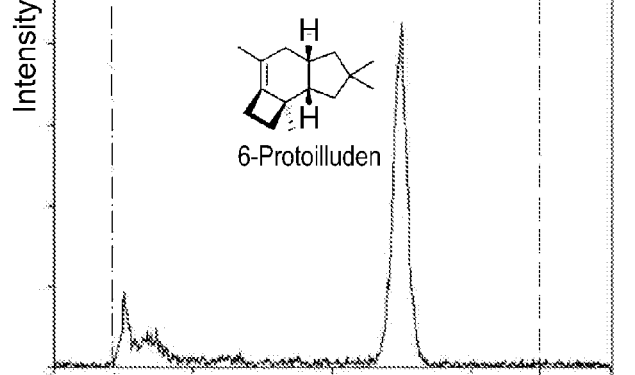
Figure 3F:
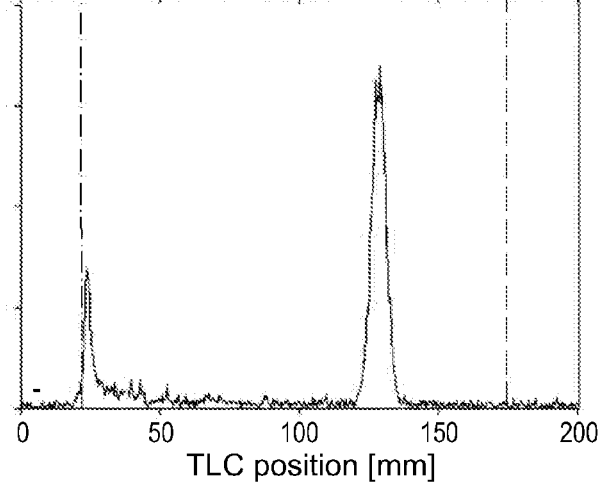

A putative honey mushroom (*Amillaria gallica*) protoilluden synthase was isolated and characterized by establishing a cell culture (FU02472) from a mushroom specimen collected near Traunsee, Austria. The culture was cultivated in liquid YM6.3 medium allowing melleolide production. After approximately 500 h of fermentation the culture was harvested and the melleolide product profile was determined by LC-UV-MS using appropriate reference substances. The major melleolides produced by FU02472 were identified as melleolide I and armillaridine (see FIG. 2).

The melleolide accumulation profile and protoilluden synthase activity were investigated over time by sampling the culture at different time points. Enzyme activity was tested by incubationg soluble enzyme extracts from the culture with radioactive-labeled farnesyl diphosphate. Organic extracts from these reactions were then analyzed by radio-TLC (see FIG. 3) Variable laveels of protoilludene synthase activity were observed in all the crude protein extracts we tested, generating a strongly non-polar product with an Rf value of 0.7 (tentatively identified as 6-protoilludene) and a product with an Rf value of 0.1 (tentatively identified as farnesol). The identity of both products was later confirmed by GC-MS (see below). Thermally-inactivated control fractions were unable to convert farnesyl diphosphate into non-polar products. The highest protoilludene synthase activity was observed after 185 h in culture, and this time point was therefore chosen for enzyme purification.

Next, it was determined whether the putative protoilludene synthase activity in the soluble protein fraction was indeed due to protoilludene synthase enzyme activity present in the fungal extract. Therefore, cold farnesyl diphosphate was spiked with tritium labeled material and incubated with the soluble protein extract from FU02472 for 12 h. The radioactive material fraction, which was then analyzed by radio-TLC and GC-MS to confirm the Rf values and identities of the products. The mass spectrum of the extracted product yielded ions at m/z 175(100%), 119(91%), 105(59%) 133(35%), 91 (40%), 189 (17%), 161 (15%) and 147 (14%) with the molecular parent ion at m/z 204 (24%). The observed fragmentation pattern matched that previously reported for the sesquiterpenoids 6-protoilludene (see FIG. 2). Surprisingly, the GC-Ms analysis did not reveal the presence of 7-protoilludene, suggesting that an allylic rearrangement from the 6(7) to the 7(8) position had occurred, as observed in the final melleolide end products. A similar allylic rearrangement has been described in the synthesis of paclitaxel for the conversion of taxa-4(5),11(12)-diene to taxa-4(20),11(12)-diene to taxa4(5), 11(12)-diene-5-ol, which is catalyzed by a cytochrome P450-dependent monooxygenase (Jennewein et al., 2004). Therefore, applicants propose that a similar cytochrome P450 dependent monooxygenase step is involved that catalyzes both the allylic rearrangement and the hydroxylation reaction during melleolide biosynthesis.

Further characterization of the enzyme was carried out using partially purified *A. gallica* protoilludene synthase, titium-labeled farnesyl diphsophate and radio-TLC analysis. These experiments revealed a $K_m$ for farnesyl diphosphate of 0.53 µM. As expected, it was found that the enzyme activity was absolutely dependent on divalent metal ions. The highest protoilludene synthase activity was achieved in the presence of 5 mM $MgCl_2$ falling by 75% when replaced with $MnCl_2$. The temperature optimum was 22° C. with nearly complete loss of activity at >35° C. Several buffering systems were tested at 50 mM, with optimal activity at pH7.2 (MOPS buffer). The activity fell by 50% at pH 5.8 (MES buffer) and pH8.5 (Tris buffer). The enzyme was also very sensitive to the presence of ethanol, with concentrations as low as 5% causing a dramatic reduction in activity.

Attempts to purify the protoilludene synthase protein of *A. gallica* to homogeneity from fungal mycelium and determine the N-terminal amino acid sequence by Edman sequencing proved unsuccessful, but showed that the enzyme was likely a 45 kDa monomer. A cDNA library was constructed from the FU02472 mycelial culture and analysis of the sequences from 2592 randomly chosen clones led to the identification of six partial sequences with homology to fugal terpene synthases, e.g. from *Coprinopsis cinerea* (*Coprinus cinereus*). Five of these sequences (two full length cDNAs, one partial cDNA and two clones containing introns) represented a single putative protoiludene sythase gene, designated Pro1. The remaining sequence, a partial cDNA approximately 600 bp in length, represented a distinct gene designated Pro2. The two putative enzymes showed approximately 55% identity at the amino acid level over ~200 residues available for comparison. Further analysis of Pro1 revealed an open reading frame 1042 bp in length, encoding a protein with 347 amino acid residues and a predicted molecular mass of 40 kDa. The Pro1 polypeptide contained DEXXD and NDxxSxxxE motifs in the appropriate orientation as is characteristic for other terpene synthases. The Pro1 amino acid sequence was used to search GenBank, revealing close relationships with the Cop3 and Cop5 sesquiterpene synthases from the basidiomycete *Coprinopsis cinerea* (32.6% and 33% identity respectively). Cop3 is a-muurolene synthase, whereas the precise function of Cop5 remains to be determined. No significant homology was observed between Pro1 and terpene synthases from ascomyceta or plants.

Heterologous expression of Pro1 in *Escherichia coli* resulted in a crude soluble protein extract possessing sufficient sesquiterpene synthase activity to convert 80% of the 0.5 μM tritium-labeled farnesyl diphosphate substrate into a product matching the properties of 6-protoilludene (Rf=0.7) within 5 min. Incubation of the same lysate with gernaylgeranyl diphosphate did not produce significant amounts of a more less polar product (<1%) and neither farnesyl diphosphate nor geranylgeranyl diphosphate were converted into less polar products when using *E. coli* control lasates derived from the empty vector control (see FIG. 3). Characterization of the heterologous teerpene synthase using cold farnesyl diphosphate, extracted with pentane and analysis of the organic extract by GC-MS revealed the formation of a product with an identical retention time and mass spectrum as the native protoiluden synthase.

Figure 4B:
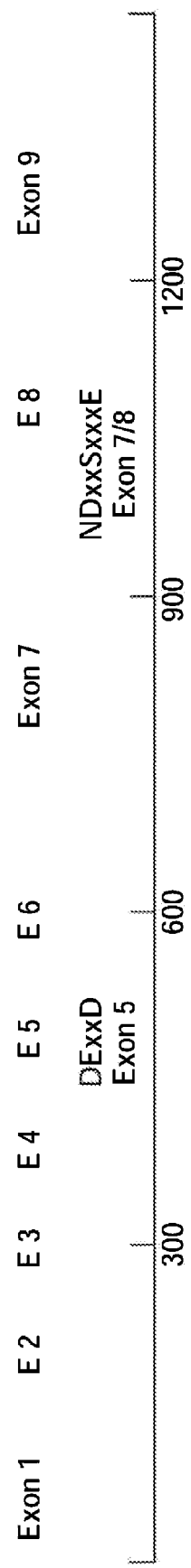
FIG. 4A is the deduced amino acid sequence alignment of fungal sesquiterpene synthases. The sequences of *A. gallica* protoilludene synthase (clone Pro1; SEQ ID No. 2), *Coprinopsis cinerea*-muurolene synthase (Cop3; SEQ ID No. 12 "Cop3") and Cop5 (a sesquiterpene synthase with yet unknown product; SEQ ID No. 13 "Cop5") are compared. Black boxes indicate identical residues for the three sequences; gray boxes indicate identical residues for two of the three sequences. 4B is a Schematic presentation of the *A. gallica* protoilludene synthase genomic sequence with exons shown as black boxes and conserved DEXXD and NDxx-SxxxE motifs.
Figure 5:
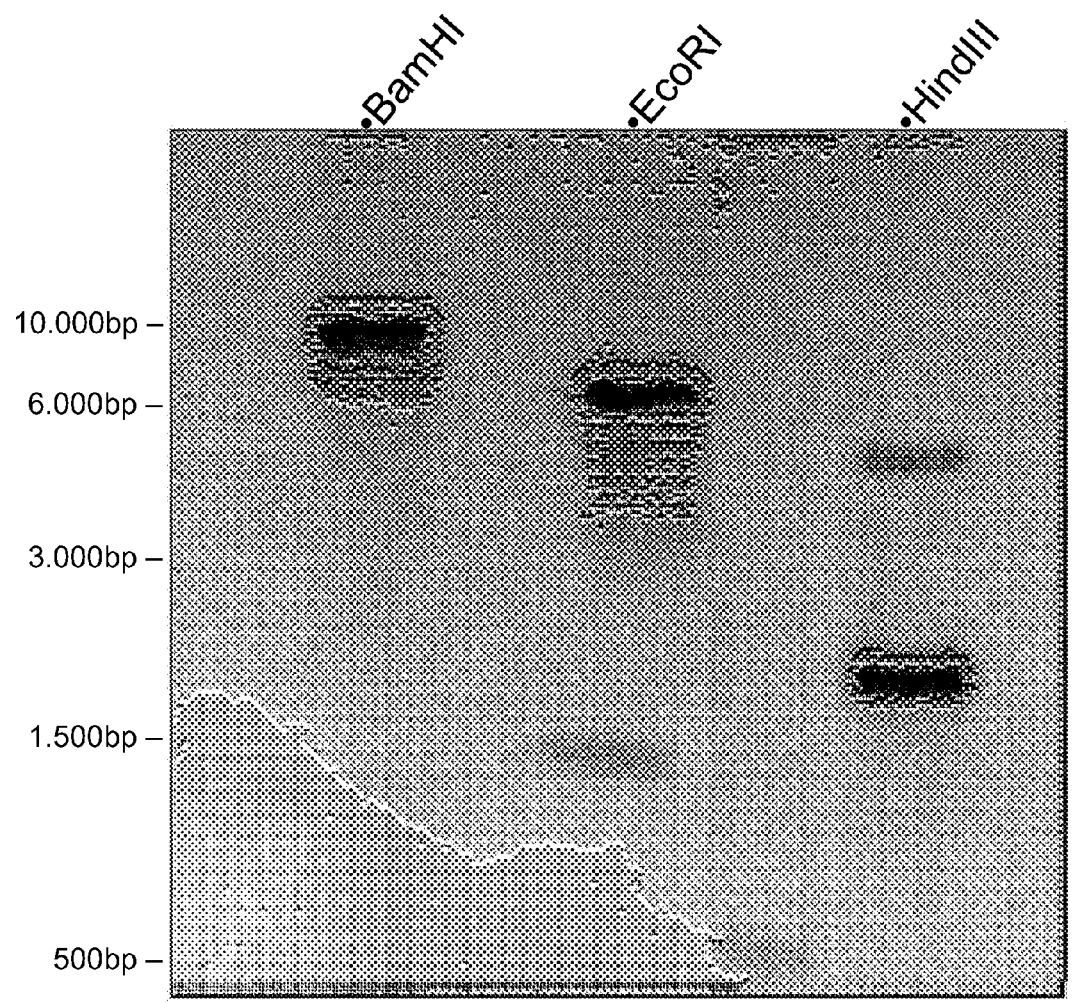
FIG. 5 shows the determination of *A. gallica* protoilludene synthase gene copy number by Southern blot hybridization. One clear band is visible in the BamHI and EcoRI lanes (neither enzyme has a target site in the genomic clone), whereas two bands are visible in the HindIII lane (there are two target sites in the clone, 85 bp apart).

The 1270 full length Pro1 cDNA clone was used to design primers allowing amplification of the corresponding genomic DNA sequence (FIG. 4.). Analysis of the 1645 bp product revealed the presence of eight introns and nine exons, some as short as 50 bp. Previous analysis of plant terpene synthases genes has revealed few introns. Southern blots, using two oligonucleotide probes representing the 5' and 3' termini of the Pro1 clone, respectively, show that there is only one copy of the Pro1 gene in the *A. gallica* genome (FIG. 5).

What is claimed is:

1. An isolated, recombinant or synthetic polynucelotide comprising a nucleic acid sequence selected from the group consisting of:
    (a) the cDNA shown in SEQ ID NO: 14 encoding a polypeptide with protoilludene synthase activity; and
    (b) a DNA complementary to SEQ ID NO: 14.

2. The polynucleotide of claim 1 consisting of the nucleic acid sequence shown in SEQ ID NO: 14.

3. An expression vector, comprising a nucleic acid sequence encoding a polypeptide with protoilludene synthase activity selected from the group consisting of
    a) the nucleic acid sequence shown in SEQ ID NO: 1;
    b) the nucleic acid sequence shown in SEQ ID NO: 14;
    c) a nucleic acid sequence encoding a polypeptide comprising the amino acid sequence set forth as SEQ ID NO: 2 wherein the nucleic acid sequence is operably linked to a promoter that is expressed by a host cell transformed with the expression vector.

4. The vector according to claim 3, wherein the vector is a viral vector.

5. The vector according to claim 3, wherein the vector is a plasmid for expression in a bacterial host cell, a cosmid, a phage, a liposome, or a virus.

6. An isolated host cell comprising the expression vector according to claim 3.

7. The isolated host cell according to claim 6, wherein the host cell is selected from the group consisting of a fungal cell, a yeast cell, a bacterial cell, an insect cell, an animal cell and a plant cell.

8. The isolated host cell according to claim 6, wherein the host cell is an *Escherichia coli* cell.

9. The isolated host cell according to claim 6, wherein the nucleic acid sequence encoding the polypeptide with protoilludene synthase activity is adapted to the codon usage of the respective cell.

10. The isolated host cell according to claim 6, wherein the host cell is a homobasidiomyceste.

11. The isolated host cell according to claim 10, characterized in that the host cell is a homobasidiomyceste of the genus *Armillaria*.

12. The isolated host cell of claim 11, wherein the host cell is an *Armillaria gallica* or a *Armillaria mellea* host cell.

13. A method for producing melleolides comprising the steps of:
(a) growing, under suitable nutrient conditions permissive for the production of the melleolides, the host cell according to claim 6; and
(b) isolating said melleolides from the host cell or the medium of its growth.

14. The method according to claim 13, wherein the melleolide is selected from melleolide I, armillaridine, melleolide A, melleolide F, melleolide B, melleolide K, armillyl evernitate, armillarin, arnamiol, melleolide J, armillarivin, 10-alpha-hydroxy-melleolide, armillyl orsellinate, melleolide E, 1-O-trifluoroacetyl-melleolide E, melleolide H, 5'-O-methyl-melledonal, melledonal, arnamial, melleolide C, melleolide D, melledonal A, melledonal C, melledonol.

15. A method for producing melleolides comprising the steps of:
i. growing in vitro, under suitable nutrient conditions in a growth medium, a host cell transformed with the expression vector of claim 5;
to overexpress the nucleic acid sequence and
enhance melleolides production in the host cell, and
ii. isolating said melleolides from the host cells or the growth medium.

* * * * *

SEQUENCE LISTING

```
<160> NUMBER OF SEQ ID NOS: 14

<210> SEQ ID NO 1
<211> LENGTH: 1659
<212> TYPE: DNA
<213> ORGANISM: Armillaria gallica
<220> FEATURE:
<221> NAME/KEY: 5'UTR
<222> LOCATION: (1)..(39)
<220> FEATURE:
<221> NAME/KEY: exon
<222> LOCATION: (40)..(156)
<220> FEATURE:
<221> NAME/KEY: exon
<222> LOCATION: (210)..(255)
<220> FEATURE:
<221> NAME/KEY: exon
<222> LOCATION: (312)..(350)
<220> FEATURE:
<221> NAME/KEY: exon
<222> LOCATION: (407)..(440)
<220> FEATURE:
<221> NAME/KEY: exon
<222> LOCATION: (492)..(538)
<220> FEATURE:
<221> NAME/KEY: exon
<222> LOCATION: (596)..(689)
<220> FEATURE:
<221> NAME/KEY: exon
<222> LOCATION: (744)..(1029)
<220> FEATURE:
<221> NAME/KEY: exon
<222> LOCATION: (1089)..(1132)
<220> FEATURE:
<221> NAME/KEY: exon
<222> LOCATION: (1183)..(1516)
<220> FEATURE:
<221> NAME/KEY: 3'UTR
<222> LOCATION: (1517)..(1659)

<400> SEQUENCE: 1
tgaccttgca gaaatcccca caccttcca ctattctca atg tct caa cgc atc      54
                                            Met Ser Gln Arg Ile
```

-continued

```
                            1               5
ttc ctt cct gat act ctt gcc aac tgg caa tgg ccc cgc cat ctc aac      102
Phe Leu Pro Asp Thr Leu Ala Asn Trp Gln Trp Pro Arg His Leu Asn
                10              15              20 ccc cac tat gcc gaa gtc aag aag gca tca gcg gcc tgg gca aaa agc      150
Pro His Tyr Ala Glu Val Lys Lys Ala Ser Ala Ala Trp Ala Lys Ser
        25              30              35 ttc cga gtaagttgga agtagaatac gtttatgtcg aatattctga ccaagagcgt      206
Phe Arg tag gct ttc caa acg aag gct cag gaa gct ttc gac cgc tgc gac ttc a   255
    Ala Phe Gln Thr Lys Ala Gln Glu Ala Phe Asp Arg Cys Asp Phe
    40              45              50 gtaagtcaag actacggcgc ttattagagc tagactgact gtacaccatc actcag at    313
                                                                Asn
                                                                55 ctc ctg gcc tca ttc gcg tac cca ctg gcg gac gaa g gcgagtgatg         360
Leu Leu Ala Ser Phe Ala Tyr Pro Leu Ala Asp Glu
            60              65 caggagaact gcccgtccat ggagcctaat ccttttttcgt ctctag ca  cgt ctc      414
                                                    Ala Arg Leu
                                                            70 cgt agc ggg tgt gat ctc atg aac ct gtaggtcttc aagccagcgc             460
Arg Ser Gly Cys Asp Leu Met Asn Leu
            75 tcggggatat tttgttgatg cgatcacaca g t ttc ttc gtt atc gac gag tac     513
                                    Phe Phe Val Ile Asp Glu Tyr
                                    80              85 tcg gac gtc tcg acg gag gag gaa g gtaagctcac cattaaattc              558
Ser Asp Val Ser Thr Glu Glu Glu
            90 tccttgagat aacagttatt ctgactgttg tatccag tg  cgc gca cag aag gac     612
                                            Val Arg Ala Gln Lys Asp
                                                95              100 ata gtc atg gat gcg att cgg aat aca gag aag cct cgg ccc gcc gga      660
Ile Val Met Asp Ala Ile Arg Asn Thr Glu Lys Pro Arg Pro Ala Gly
                105             110             115 gag tgg att gga gga gaa gta tct cga ca  gtcagtacca cacatttaga        709
Glu Trp Ile Gly Gly Glu Val Ser Arg Gln
        120             125 tacccatgat ccatggactg atcgtacgct atag a ttc tgg gac ctc gca aag      762
                                        Phe Trp Asp Leu Ala Lys
                                                130 aag aca gcg agc act caa gcg cag aag cgc ttc atc gac acc ttc gac      810
Lys Thr Ala Ser Thr Gln Ala Gln Lys Arg Phe Ile Asp Thr Phe Asp
        135             140             145 gag tac ctg gag tct gtc gta caa cag gcc gcc gac cgc aac aac tcc      858
Glu Tyr Leu Glu Ser Val Val Gln Gln Ala Ala Asp Arg Asn Asn Ser
        150             155             160 cac gtc cga ggc atc gag tcg tac ctc gaa gtt cgc cgc aac acc atc      906
His Val Arg Gly Ile Glu Ser Tyr Leu Glu Val Arg Arg Asn Thr Ile
165             170             175             180 ggc gcg aaa cca tcg ttc gca ctt ctc gag ttt gac atg cag tta ccc      954
Gly Ala Lys Pro Ser Phe Ala Leu Leu Glu Phe Asp Met Gln Leu Pro
            185             190             195 gac gaa agt cat caa tca tcc ggt tat caa aga aac ttg aga aag agc      1002
Asp Glu Ser His Gln Ser Ser Gly Tyr Gln Arg Asn Leu Arg Lys Ser
            200             205             210 tgt att gat atg ctc tgc ttg gga aac gtgagcaatc cgtctttatc            1049
Cys Ile Asp Met Leu Cys Leu Gly Asn
```

```
                                -continued
         215                 220
caccacagaa aaagggaact gacctcttat actttcaag gat gtc gtt tcg tat        1103
                                            Asp Val Val Ser Tyr
                                                            225 aac ctt gaa caa gct cgg gat gac gac gg  gtgagtcttt agcatttcgc        1152
Asn Leu Glu Gln Ala Arg Asp Asp Asp Gly
        230                 235 ccgtcattat cattctgacg cggtctctag c cac aac atc gtc act atc gca        1204
                                  His Asn Ile Val Thr Ile Ala
                                                          240 atg aac gag ctc agg aca gac gtg gca ggt gcc atg att tgg gtc gac      1252
Met Asn Glu Leu Arg Thr Asp Val Ala Gly Ala Met Ile Trp Val Asp
    245                 250                 255 gaa tac cac aag cag ctc gag tcc agg ttc atg gaa aac ttc aag aaa      1300
Glu Tyr His Lys Gln Leu Glu Ser Arg Phe Met Glu Asn Phe Lys Lys
260                 265                 270                 275 gtg ccc aga tgg gga ggt ccc att gac ctg cag gtt gct cga tac tgt      1348
Val Pro Arg Trp Gly Gly Pro Ile Asp Leu Gln Val Ala Arg Tyr Cys
                280                 285                 290 gat ggg cta ggt aat tgg gtg aga gcg aat gac cag tgg agc ttc gag      1396
Asp Gly Leu Gly Asn Trp Val Arg Ala Asn Asp Gln Trp Ser Phe Glu
            295                 300                 305 agc gag aga tac ttt gga aag aag ggt cca gaa atc atc cag agg agg      1444
Ser Glu Arg Tyr Phe Gly Lys Lys Gly Pro Glu Ile Ile Gln Arg Arg
        310                 315                 320 tgg ata acg ctg atg ccc aag atg gtg tcg gag gaa ctt ggt cct caa      1492
Trp Ile Thr Leu Met Pro Lys Met Val Ser Glu Glu Leu Gly Pro Gln
    325                 330                 335 att gtt gac gga ttt cat ctc tag cgagtacgtt tgcgctgtat atattatata    1546
Ile Val Asp Gly Phe His Leu
340                 345 ttagggtaga gtaaattagt ttcgaggaat atttcccagt gtagacggtg tagatgacaa    1606
gtagatggac ttcgaatttg aaacagccca ttacacatgt ttggcaaagg cct           1659

<210> SEQ ID NO 2
<211> LENGTH: 346
<212> TYPE: PRT
<213> ORGANISM: Armillaria gallica

<400> SEQUENCE: 2

Met Ser Gln Arg Ile Phe Leu Pro Asp Thr Leu Ala Asn Trp Gln Trp
1               5                   10                  15

Pro Arg His Leu Asn Pro His Tyr Ala Glu Val Lys Lys Ala Ser Ala
            20                  25                  30

Ala Trp Ala Lys Ser Phe Arg Ala Phe Gln Thr Lys Ala Gln Glu Ala
        35                  40                  45

Phe Asp Arg Cys Asp Phe Asn Leu Leu Ala Ser Phe Ala Tyr Pro Leu
    50                  55                  60

Ala Asp Glu Ala Arg Leu Arg Ser Gly Cys Asp Leu Met Asn Leu Phe
65                  70                  75                  80

Phe Val Ile Asp Glu Tyr Ser Asp Val Ser Thr Glu Glu Val Arg
            85                  90                  95

Ala Gln Lys Asp Ile Val Met Asp Ala Ile Arg Asn Thr Glu Lys Pro
        100                 105                 110

Arg Pro Ala Gly Glu Trp Ile Gly Gly Glu Val Ser Arg Gln Phe Trp
    115                 120                 125

Asp Leu Ala Lys Lys Thr Ala Ser Thr Gln Ala Gln Lys Arg Phe Ile
```

-continued

```
                130                 135                 140
Asp Thr Phe Asp Glu Tyr Leu Glu Ser Val Val Gln Gln Ala Ala Asp
145                 150                 155                 160

Arg Asn Asn Ser His Val Arg Gly Ile Glu Ser Tyr Leu Glu Val Arg
                165                 170                 175

Arg Asn Thr Ile Gly Ala Lys Pro Ser Phe Ala Leu Leu Glu Phe Asp
            180                 185                 190

Met Gln Leu Pro Asp Glu Ser His Gln Ser Ser Gly Tyr Gln Arg Asn
        195                 200                 205

Leu Arg Lys Ser Cys Ile Asp Met Leu Cys Leu Gly Asn Asp Val Val
    210                 215                 220

Ser Tyr Asn Leu Glu Gln Ala Arg Asp Asp Gly His Asn Ile Val
225                 230                 235                 240

Thr Ile Ala Met Asn Glu Leu Arg Thr Asp Val Ala Gly Ala Met Ile
                245                 250                 255

Trp Val Asp Glu Tyr His Lys Gln Leu Glu Ser Arg Phe Met Glu Asn
                260                 265                 270

Phe Lys Lys Val Pro Arg Trp Gly Pro Ile Asp Leu Gln Val Ala
            275                 280                 285

Arg Tyr Cys Asp Gly Leu Gly Asn Trp Val Arg Ala Asn Asp Gln Trp
    290                 295                 300

Ser Phe Glu Ser Glu Arg Tyr Phe Gly Lys Lys Gly Pro Glu Ile Ile
305                 310                 315                 320

Gln Arg Arg Trp Ile Thr Leu Met Pro Lys Met Val Ser Glu Glu Leu
                325                 330                 335

Gly Pro Gln Ile Val Asp Gly Phe His Leu
            340                 345

<210> SEQ ID NO 3
<211> LENGTH: 24
<212> TYPE: DNA
<213> ORGANISM: Artificial
<220> FEATURE:
<223> OTHER INFORMATION: Primer

<400> SEQUENCE: 3
ctcgcgttaa cgctagcatg gatg                                          24

<210> SEQ ID NO 4
<211> LENGTH: 27
<212> TYPE: DNA
<213> ORGANISM: Artificial
<220> FEATURE:
<223> OTHER INFORMATION: Primer

<400> SEQUENCE: 4
gtgagtcgta ttacatggtc atagctg                                       27

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5
cgacggccag tcttaagctc gggc                                          24

<210> SEQ ID NO 6
```

```
<211> LENGTH: 24
<212> TYPE: DNA
<213> ORGANISM: Artificial
<220> FEATURE:
<223> OTHER INFORMATION: Primer

<400> SEQUENCE: 6
ccttcctgat actcttgcca actg                                              24

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
cctcctccgt cgagacgtcc gagtac                                            26

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
gtcatcaatc atccggttat caaag                                             25

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
cttgggcatc agcgttatcc acctc                                             25

<210> SEQ ID NO 10
<211> LENGTH: 71
<212> TYPE: DNA
<213> ORGANISM: Artificial
<220> FEATURE:
<223> OTHER INFORMATION: Primer

<400> SEQUENCE: 10
ggggacaagt ttgtacaaaa aagcaggctt cgaaggagat agaaccatgt ctcaacgcat       60
cttccttcct g                                                            71

<210> SEQ ID NO 11
<211> LENGTH: 59
<212> TYPE: DNA
<213> ORGANISM: Artificial
<220> FEATURE:
<223> OTHER INFORMATION: Primer

<400> SEQUENCE: 11
ggggaccact ttgtacaaga aagctgggtt tagagatgaa atccgtcaac aatttgagg        59

<210> SEQ ID NO 12
<211> LENGTH: 425
<212> TYPE: PRT
<213> ORGANISM: Coprinus cinereus

<400> SEQUENCE: 12
```

```
Met Ser Thr Pro Ser Ser Leu Thr Thr Asp Glu Ser Pro Ala Ser
1               5                   10                  15

Phe Ile Leu Pro Asp Leu Val Ser His Cys Pro Phe Pro Leu Arg Tyr
                20                  25                  30

His Pro Lys Gly Asp Glu Val Ala Lys Gln Thr Val His Trp Leu Asp
            35                  40                  45

Ser Asn Cys Pro Asp Leu Thr Ala Lys Glu Arg Lys Ala Met Tyr Gly
        50                  55                  60

Leu Gln Ala Gly Glu Leu Thr Gly Tyr Cys Tyr Pro Tyr Thr Thr Pro
65                  70                  75                  80

Glu Arg Leu Arg Val Val Ala Asp Phe Leu Asn Tyr Leu Phe His Leu
                85                  90                  95

Asp Asn Ile Ser Asp Gly Met Met Thr Arg Glu Thr Ala Val Leu Ala
            100                 105                 110

Asp Val Val Met Asn Ala Leu Trp Phe Pro Glu Asp Tyr Arg Pro Thr
        115                 120                 125

Lys Gly Gln Ala Ala Glu Glu Leu Asn Pro Gly Lys Leu Ala Arg Asp
130                 135                 140

Phe Trp Ser Arg Cys Ile Pro Asp Cys Gly Pro Gly Thr Gln Ala Arg
145                 150                 155                 160

Phe Lys Glu Thr Phe Gly Ser Phe Phe Glu Ala Val Asn Ile Gln Ala
                165                 170                 175

Arg Ala Arg Asp Glu Gly Val Ile Pro Asp Leu Glu Ser Tyr Ile Asp
            180                 185                 190

Val Arg Arg Asp Thr Ser Gly Cys Lys Pro Cys Trp Val Leu Ile Glu
        195                 200                 205

Tyr Ala Leu Gly Ile Asp Leu Pro Asp Phe Val Val Glu His Pro Val
210                 215                 220

Ile Ala Ala Leu Asn Gln Gly Thr Asn Asp Leu Val Thr Trp Ser Asn
225                 230                 235                 240

Asp Ile Phe Ser Tyr Asn Val Glu Gln Ser Lys Gly Asp Thr His Asn
                245                 250                 255

Met Ile Ile Ile Leu Met Glu His His Gly His Thr Leu Gln Ser Ala
            260                 265                 270

Val Asp Tyr Val Gly Ser Leu Cys Gln Gln Thr Ile Asn Thr Phe Cys
        275                 280                 285

Glu Asn Lys Gln Gln Leu Pro Ser Trp Gly Pro Glu Ile Asp Asp Met
290                 295                 300

Val Ala Lys Tyr Val Gln Gly Leu Glu Asp Trp Ile Val Gly Ser Leu
305                 310                 315                 320

His Trp Ser Phe Gln Thr Arg Arg Tyr Phe Gly Asp Glu Gly Gln Glu
                325                 330                 335

Ile Lys Gln His Arg Leu Val Lys Leu Leu Thr Val Ala Pro Pro Pro
            340                 345                 350

Pro Pro Pro Pro Pro Thr Pro Pro Gln Ser Ser Asp Ala Asp Thr
        355                 360                 365

Lys Lys Gln Lys Val Lys Ala Gln Asp Gly Lys Gly Pro Val Ser Asp
370                 375                 380

Glu Glu Val Trp Ala Leu Val Arg Ala Glu Gln Ser Lys Gly Ser Ile
385                 390                 395                 400

Leu Glu Ser Leu Phe Gly Phe Leu Thr Thr Ser Leu Ser Arg Ile Phe
                405                 410                 415
```

```
Phe Gly Tyr Phe Ala Tyr Ser His
        420             425
```

<210> SEQ ID NO 13
<211> LENGTH: 330
<212> TYPE: PRT
<213> ORGANISM: Coprinus cinereus
<400> SEQUENCE: 13

```
Met Val Gly Ser Tyr Thr Gly Lys Val Ile His Val Pro Ala Leu Leu
1               5                   10                  15

Glu Ser Trp Pro Trp Pro Ala Ala Ile Asn Pro Leu Tyr Glu Gln Val
            20                  25                  30

Gln Glu Glu Ser Thr Ser Trp Phe Arg Lys Phe Asp Leu Tyr Arg Asp
        35                  40                  45

Arg Lys Lys Gln Ala Ile His Asp His Leu Asp Thr Ala Lys Phe Gly
    50                  55                  60

Ala Ser Val Cys Pro Lys Ala Asp Tyr Ala Leu Leu Arg Leu Ala Thr
65                  70                  75                  80

Asp Tyr Leu His Leu Gly Phe Trp Ile Asp Tyr Phe Phe Asp Thr Ser
                85                  90                  95

Pro Ser Asp Val Ile Arg Gln Leu Thr Glu Ser Ile Ala His Leu Leu
            100                 105                 110

Glu Ser Gly Asp Pro Arg Leu Asp Ser Ser Pro Gln Ser His Ile
        115                 120                 125

Ala Cys Met Glu Ile Leu Arg Asp Phe Arg Lys Arg Ile Glu Thr Phe
    130                 135                 140

Asn Pro Ser Gln Glu Asp Leu Arg Arg Phe Val Lys Glu Tyr Arg Gly
145                 150                 155                 160

Phe Leu Glu Ala Glu Leu Thr Gln Ala Ile Asp His Glu Asn Lys Val
                165                 170                 175

Ile Arg Asp Ile Glu Ser Tyr Leu Ser Ile Arg Arg Ser Thr Ile Ala
            180                 185                 190

Ile Arg Pro Gly Ile Ala Leu Leu Gly Leu Ala Leu Gly Ile Pro Gln
        195                 200                 205

Glu Ile Leu Asp Asp Pro Tyr Thr Asp Thr Leu Thr Asn Ala Cys Leu
    210                 215                 220

Asp Met Val Ile Ile Gln Asn Asp Ala Tyr Ser Trp Asn Val Glu Gln
225                 230                 235                 240

Val Arg Lys Ala Asp Gly His Asn Ile Ile Thr Val Leu Met Lys Gln
                245                 250                 255

Arg Asp Ile Asp Val Gln Glu Ala Tyr Glu His Ala Ala Gln Leu His
            260                 265                 270

Arg Glu Thr Gln Glu His Phe Leu Glu Leu His Ala Lys Arg Pro Asp
        275                 280                 285

Trp Gly Asn Glu Gly Ser Ile Gln Ala Phe Phe Asp Gly Leu Gly Glu
    290                 295                 300

Phe Val Arg Gly Val Asp Glu Trp Ser Ser Met Cys Leu Gly Glu His
305                 310                 315                 320

Ala Leu Ser Val Gly Ala Gly Phe Leu Lys
                325                 330
```

<210> SEQ ID NO 14
<211> LENGTH: 1223
<212> TYPE: DNA
<213> ORGANISM: Armillaria gallica -continued

```
<220> FEATURE:
<221> NAME/KEY: 5'UTR
<222> LOCATION: (1)..(39)
<220> FEATURE:
<221> NAME/KEY: 3'UTR
<222> LOCATION: (1081)..(1223)

<400> SEQUENCE: 14
tgaccttgca gaaatcccca caccctccca ctattctcaa tgtctcaacg catcttcctt    60
cctgatactc ttgccaactg gcaatggccc cgccatctca accccacta tgccgaagtc   120 aagaaggcat cagcggcctg ggcaaaaagc ttccgagctt tccaaacgaa ggctcaggaa   180
gctttcgacc gctgcgactt caatctcctg gcctcattcg cgtacccact ggcggacgaa   240
gcacgtctcc gtagcgggtg tgatctcatg aaccttttct tcgttatcga cgagtactcg   300
gacgtctcga cggaggagga agtgcgcgca cagaaggaca tagtcatgga tgcgattcgg   360
aatacagaga agcctcggcc cgccggagag tggattggag gagaagtatc tcgacaattc   420
tgggacctcg caaagaagac agcgagcact caagcgcaga agcgcttcat cgacaccttc   480
gacgagtacc tggagtctgt cgtacaacag gccgccgacc gcaacaactc ccacgtccga   540
ggcatcgagt cgtacctcga agttcgccgc aacaccatcg gcgcgaaacc atcgttcgca   600
cttctcgagt ttgacatgca gttacccgac gaaagtcatc aatcatccgg ttatcaaaga   660
aacttgagaa agagctgtat tgatatgctc tgcttgggaa acgatgtcgt ttcgtataac   720
cttgaacaag ctcgggatga cgacggccac aacatcgtca ctatcgcaat gaacgagctc   780
aggacagacg tggcaggtgc catgatttgg gtcgacgaat accacaagca gctcgagtcc   840
aggttcatgg aaaacttcaa gaaagtgccc agatggggag gtcccattga cctgcaggtt   900
gctcgatact gtgatgggct aggtaattgg gtgagagcga atgaccagtg gagcttcgag   960
agcgagagat actttggaaa gaagggtcca gaaatcatcc agaggaggtg gataacgctg  1020
atgcccaaga tggtgtcgga ggaacttggt cctcaaattg ttgacggatt tcatctctag  1080
cgagtacgtt tgcgctgtat atattatata ttagggtaga gtaaattagt ttcgaggaat  1140
atttcccagt gtagacggtg tagatgacaa gtagatggac ttcgaatttg aaacagccca  1200
ttacacatgt ttggcaaagg cct                                         1223
```